United States Patent
Renda

(10) Patent No.: US 6,197,334 B1
(45) Date of Patent: Mar. 6, 2001

(54) LOZENGE AND METHOD OF MAKING

(76) Inventor: Donald V. Renda, 109 E. South Temple #2B, Salt Lake City, UT (US) 84111

( * ) Notice: Subject to any disclaimer, the term of this patent is extended or adjusted under 35 U.S.C. 154(b) by 0 days.

(21) Appl. No.: 09/291,134

(22) Filed: Apr. 12, 1999

Related U.S. Application Data

(60) Provisional application No. 60/081,717, filed on Apr. 13, 1998.

(51) Int. Cl.⁷ ........................................ A61K 9/20
(52) U.S. Cl. .................. 424/464; 424/435; 424/441; 424/465; 514/772.3; 514/783; 514/784; 514/785; 514/786
(58) Field of Search ...................... 424/435, 441, 424/440, 464, 465

(56) References Cited

U.S. PATENT DOCUMENTS 3,920,849 * 11/1975 Marmo et al. ............................ 426/3
4,752,479 * 6/1988 Briggs et al. ......................... 424/472

\* cited by examiner

*Primary Examiner*—James M. Spear
(74) *Attorney, Agent, or Firm*—Workman, Nydegger & Seeley

(57) ABSTRACT

A device for delivering a liquid, semiliquid or solid beneficial agent into the mouth of a human or animal is disclosed. The device has a size and shape adapting it to be comfortably retained in the mouth for extended periods of time. The device may be formulated in one of two forms: 1) one form comprises a wall surrounding a hollow compartment holding the beneficial agent. A passageway in the wall connects the agent with the exterior of the device. The wall is impermeable and, with the exception of the passageway, fluids may not enter into the hollow compartment, or escape from the hollow compartment into the mouth. The size and configuration of the passageway determines the rate at which the agent is released into the mouth. Pressure on the device, such as sucking, squeezing or chewing, also influences the rate at which the agent is released into the mouth, and 2) the other form is comprised of combining a beneficial agent with a unique, solid mixture that allows the beneficial agent to be slowly released into the mouth. Pressure on the device, such as sucking, squeezing or chewing, influences the rate at which the agent is released into the mouth.

34 Claims, 2 Drawing Sheets

LOZENGE AND METHOD OF MAKING

This is a U.S. Patent Application claims priority to U.S. Provisional Patent Application Ser. No. 60/081,717, filed on Apr. 13, 1998, which is incorporated herein by reference.

BACKGROUND OF THE INVENTION

1. The Field of the Invention

The present invention is related to modalities for the mammalian administration of medicaments.

2. The Relevant Technology

Devices for delivering beneficial agents into the mouth of humans or animals have been sought after since recorded history. There are many medical conditions that would benefit from a device that would deliver a medication into the buccal cavity over an extended period of time. There are many devices that have been utilized from time to time with varying degrees of success. Most of these devices fall into the following categories: 1) Osmosis controlled devices, 2) Erosion controlled devices, 3) Diffusion controlled devices, 4) pH controlled devices, 5) Shrink polymer controlled devices, and 6) Pump controlled devices. Each method has its' merits and each method has its' shortcomings.

Recently, numerous advancements have taken place in the field of pharmacology and pharmaceutics with respect to the administration of drugs to treat various conditions. Despite the tremendous advancements in the field, however, drugs continue to be administered using substantially the same techniques that have been used for many decades. The vast majority of pharmaceutical agents continue to be administered either orally or by injection. Nevertheless, it is frequently found in the art that neither of these administration routes are effective in all cases, and both administration routes suffer from several disadvantages.

Oral administration is probably the most prevalent method of administering pharmacological medicaments. The medicament is generally incorporated into a tablet, capsule, or a liquid base, and then swallowed. The oral administration modality is often preferred because of its convenience. In addition, oral administration is Generally non-threatening, painless and simple to accomplish for most patients.

Nevertheless, oral administration of drugs suffers from several disadvantages. One disadvantage is that pediatric and geriatric patients frequently have difficulty swallowing pills and other solid dosage forms, and such patients often refuse to cooperate in swallowing liquid medication. In addition, for many medicaments, the act of swallowing the medicament often requires fluids that increase gastric volume and the likelihood of nausea and vomiting is also increased.

A further problem with oral administration is that the amount of the drug that gets into the bloodstream after swallowing varies from patient to patient. The absorption of the drug is dependent upon the movement of the drug from the stomach to the small and large intestines; the effects of secretions from these organs and the resulting pH within the stomach and intestines also influence the absorption. Anxiety and stress can dramatically reduce these movements and secretions preventing or reducing the final effects of the drug, and may delay the onset of the drug's effects.

Most significant is the fact that there is normally substantial delay between the time of oral administration and the time that the therapeutic effect of the drug begins. As mentioned above, the drug must pass through the gastrointestinal system in order to enter the bloodstream; this typically takes forty-five minutes or longer. As mentioned above, anxiety and stress often increase this delay.

For many applications, such as premedication before surgery or where immediate relief from pain or a serious medical condition or immediate effectiveness of the drug is required, this delay is unacceptable. In modern outpatient units and operating rooms where rapid turnover of patients is essential for cost containment, extensive delays in the action of a drug are simply unacceptable.

An additional disadvantage of oral administration is that many drugs almost immediately experience metabolism or inactivation. The veins from the stomach and the small and large intestines pass directly through the liver. Thus, drugs entering the bloodstream must first pass through the liver before distribution into the general blood circulation. More than sixty percent of most drugs (and essentially one hundred percent of certain drugs) are removed from the patient's bloodstream during this "first pass" through the liver. The result is that oral administration is impractical for many drugs, particularly many central nervous system and many cardiovascular-acting drugs that are used for rapid onset in critical care situations, as a premedication prior to surgery, or for the induction of anesthesia.

Further, additional stress is placed on the liver as it removes the excess drug from the bloodstream. This is particularly severe if the drug treatment has been occurring over an extended period of time. The liver may become overloaded with the drugs' metabolites which then must be excreted. As a result, there is an increased risk of hepatic or renal disorders.

Another difficulty encountered in administering drugs orally is that dosages are prepared or determined for use with an "average" patient. Most drugs have widely varying effects on different patients. These effects depend upon patient habits, subtle genetic differences between patients, blood volumes, age, and numerous other known and unknown factors. Introducing a drug orally does not provide the ability to control the precise dose needed to obtain the desired effect, rather the dose is estimated in order to produce an average effect in an average patient. The result may be underdosing or overdosing a particular patient.

Underdosing a patient because of a low susceptibility to the drug fails to evoke the response sought by the physician. Overdosing the patient can result in dangerous depression of vital body functions, especially the heart and lungs. This can cause prolonged respiratory depression (necessitating mechanical ventilation after surgery), cardiac depression, and arrest.

In order to avoid some of the disadvantages of oral administration, injection is frequently used, Injecting a drug (generally intravenously or intramuscularly), results in rapid entry of the drug into the patient's bloodstream. In addition, this type of delivery avoids the removal of large quantities of the drug by the patient's liver. As a result, less total drug is usually needed compared to orally administered drugs. The drug instead becomes rapidly distributed to various portions of the patient's body before exposure to the liver.

Most patients, particularly children and geriatric adults have an aversion to injections. In some patients, this aversion may be so pronounced as to make the use of injections a serious concern. Since intense psychological stress can exacerbate a patient's debilitated condition, it sometimes becomes undesirable to use injections where the patient is seriously ill or suffers from a debilitating condition or injury.

In addition, individual variations in susceptibility in the metabolism of various drugs (particularly drugs with central nervous system activity) are even more profound when utilizing the injection route. In many instances to prevent overdosing, it is the practice to inject a patient with a lower than average dose and then supplement the dose with additional injections as necessary. This "titration" makes necessary the use of repeated injections, which in turn greatly increases stress on the patient. Again, a precise dose cannot be administered to produce a precise effect because the patient's response varies widely depending on the specific characteristics of the patient.

One common approach to preparing a patient for surgery is to orally administer a sedative or an antianxiety drug. Although quick onset of sedation or anxiolysis has not always been a critical factor, it is more so now. Changing practices, including the increased use of outpatient units for day surgery and the pressures for cost containment in modern medicine, dictate rapid onset of action and the use of an absolutely ideal dose in order to avoid increased costs of caring for patients with delayed recovery secondary to slightly overdosing with anesthesia. Effective oral administration of premedication drugs with central nervous system activity (which cause a rapid onset of sedation and anxiolysis without producing excessive sedation) is often difficult to accomplish.

Some investigators have suggested that it may be possible to administer medication through the buccal mucosa of the check pouch or by sublingual administration. See, U.S. Pat. No. 4,671,953 entitled "METHODS AND COMPOSITIONS FOR NONINVASIVE ADMINISTRATION OF SEDATIVES, ANALGESICS, AND ANESTHETICS." Such administration through the mucosal tissues of the mouth, pharynx, and esophagus of therapeutic drugs possesses a distinct usefulness. Administration of drugs by this route does not expose the drug to the gastric and digestive juices. In addition the drugs largely bypass the liver on the first pass through the body, thereby avoiding additional metabolism and/or inactivation of the drug.

Generally the drugs which are administered by any of the methods described above have an unpleasant taste. As a result, in order to allow for buccal or sublingual administration through the oral mucosal tissues, it is also necessary to incorporate the drug into some type of pleasant tasting agent. While the administration of certain drugs through the oral mucosal tissues has shown promise, development of a fully acceptable method for producing a medication in a desirable form and administering the medication has been elusive. It has not been possible to develop an acceptable candy product for use with most drugs without heating the product to the point where degradation will be expected.

It should also be noted that pH conditions within the mouth may tend to adversely affect the effectiveness of certain drugs. It has been found in the art that administration of drugs through the mucosal tissues generally occurs best when the drug is in the unionized form; the unionized portion of the drug is usually lipid soluble (lipophilic) and can readily diffuse through the cell membrane. The ionized portion of the drug, conversely, is often lipid insoluble (nonlipophilic) and in most cases may not efficiently penetrate the lipid membrane of the cell. Drugs in the ionized form are generally inefficient in producing a drug effect on the central nervous system, the cardiovascular system or the renal vascular system. Variations in pH affect the percentage of the drug which is unionized at a particular point in time. As a result, the pH conditions within the mouth often limit the effectiveness of certain drugs administered buccally or sublingually in that those conditions cause the drug to exist in a form which is largely unavailable for transfer across the mucosal tissues.

Other potent drugs are substantially nonlipophilic and do not naturally permeate mucosal tissues. Hence it would be a significant advancement in the art of administering potent, fast acting drugs, if suitable methods and compositions permitted both lipophilic and nonlipophilic drugs to be administered transmucosally.

It would be another important advancement in the art of administering potent, fast-acting drugs, if suitable methods and compositions provided a precise dosage to a precise effect in every patient. A related advancement in the art would be to provide such methods and compositions that would avoid the disadvantages of overdosing, and the immediate metabolism encountered in the "first pass effect", yet do not involve injection by needle into the patient.

Many people suffer from a very serious medical condition called obesity. The definition of obesity is when an individual is 20% over that individuals normal weight. It is estimated that approximately 20% of the adult U.S. population suffers from obesity. World wide obesity approaches approximately 15%; the lower percentage is no doubt due to lower caloric laden foods in less affluent countries. The normal caloric intake for an adult man is approximately 2500 calories per day. The normal caloric intake for an adult woman is approximately 2000 calories per day. If the number of calories consumed over a 24 hour period of time equals the number of calories expended over a 24 hour period of time, an individuals'weight will stay the same. If the number of calories consumed over a 24 hour period of time is greater than the number of calories expended over a 24 hour period of time, an individuals'weight will increase as the excess calories are converted to fat and stored in the body. If the number of calories consumed over a 24 hour period of time is less than the number of calories expended, an individuals'weight will decrease as the deficit in calories consumed will cause fat stored in the body to be converted into calories to make up for the deficit in calorie intake. Thus, over a long period of time, excess caloric intake will cause an individual to become fat and possibly even obese. Also, over a long period of time, a deficit in calory intake will cause an individual to become thin as the body mobilizes and burns body fat to compensate for the deficit in caloric intake. Most nutritionists agree that three balanced, nutritious meals a day provide sufficient protein, carbohydrates, fat, vitamins and minerals for normal body function. Most individuals that suffer from an overweight condition or even from obesity have difficulty eating only three meals daily. These individuals have a tendency to eat between meals. This condition is called snacking and many of these snack foods are high calorie in content.

Thus, there is clearly a need for a device that will take away the desire to snack in between regular meals. This device would be a substitute for snack foods and offer a low or non-calorie alternative to high calorie snack foods. The device would also be designed to have a mode of action that would provide for a sustained or prolonged alternative to snack food.

There is clearly a need for a simple, economical device that will deliver a sustained release of beneficial agent into the oral cavity.

SUMMARY AND OBJECTS OF THE INVENTION

It is, accordingly, an immediate object of this invention to provide a dispensing device for the controlled, extended delivery of a beneficial agent, and which device represents an improvement and an advancement in the agent delivery arts.

This invention relates to a device to be used for administering potent, fast acting drugs and other substances transmucosally. In use, the present invention provides for the administration of drugs and other substances through the mucosal tissue of the mouth, pharynx and esophagus, thereby avoiding the problems of both injection and oral administration.

An important object of the invention, wherein a drug is released from a nondissolvable drug containment device, is that the drug is administered through the oral mucosal tissues and will quickly enter the patient's bloodstream through the veins which serve these tissues. Employing the present invention, the drug may be introduced into the patient's bloodstream almost as fast as through injection, and much faster than using the oral route, while avoiding the negative aspects of both methods.

Another important feature within the scope of the present invention is the ability to use a wide variety of beneficial agents or drugs.

Still another important object is that the active ingredient may be enhanced by the use of flavorings, colorings, sweeteners, buffering forming agents and permeation enhancing agents in order to present the drug for transmucosal delivery.

A further advantage of the present invention is that flexibility is enhanced by the ability to add drugs (or combinations of drugs), flavors (or combinations of flavors), buffer forming agents and other types of pH control; and that they can be added simultaneously in order to provide for maximum drug efficiency and efficacy. It will be appreciated that drugs in the unionized form are more readily transported across the mucosal membrane. Therefore, if pH conditions can be adjusted to maximize the percentage of unionized drug available, the effectiveness of the drug is maximized. Buffering agents are particularly important for those drugs that partially ionize within the pH range of the mouth, such as weak acid and weak base drugs. Generally, buffering agents are more important when hydrophilic drugs are used because those drugs usually have lower mucosal permeability and dissolve more readily in saliva within the mouth.

It is a further object of the present invention to provide methods and compositions for administering potent, fast-acting drugs, which administer a precise dosage to obtain a precise effect in every patient. A dosage-form within the scope of the present invention can be used to administer drugs in a dose-to-effect manner, or until the precise effect is achieved.

Another object of the invention is to facilitate monitoring of the patient's reaction to the drugs which have an observable or monitorable effect such as a drug effecting the central nervous, cardiovascular, respiratory, or renal vascular systems. When the drug has evoked a suitable response, the dosage-form may then be removed, or its rate of consumption may be modified in order to maintain the desired effect. It will be appreciated that the ever present risk of overdosing a patient is substantially minimized through the use of the present invention. According to the present invention, the drug dose is given over a period of time rather than all at once, and the administration rate can be adjusted if it appears to be necessary. Once a sufficient drug response has been achieved, the patient can simply stop sucking or squeezing the device or the patient or medical professional can easily remove the device from the patient's mouth.

Another object of the present invention is to provide suitable methods and compositions for the noninvasive transmucosal administration of both lipophilic and nonlipophilic drugs. A related object of the present invention is the use of suitable permeation enhancers which improve drug permeation across the mucosal membrane. Both nonlipophilic and lipophilic drugs may be improved by using suitable permeation enhancers.

A related object of the present invention is to provide such methods and compositions that avoid the disadvantages of overdosing, underdosing, and the immediate metabolism encountered in the "first pass effect," yet do not involve injection by needle into the patient.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only typical embodiments of the invention and are not therefore to be considered to be limiting of its scope, the invention will be described and explained with additional specificity and detail through the use of the accompanying drawings in which the drawing figures, which are not drawn to scale, set forth various embodiments of the present invention where the figures are as follows.

DETAILED DESCRIPTION OF THE DRAWINGS

Figure 1:
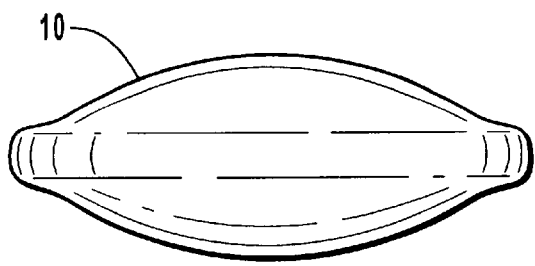
FIG. 1 is a general side view of a device for dispensing a beneficial agent into the oral cavity. Both hollow and solid forms are shown.
Figure 2:
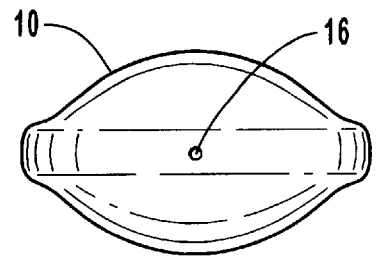
FIG. 2 is a general end view of the hollow form including a view of the opening of the passageway leading to the exterior, of a device for dispensing a beneficial agent into the oral cavity.
Figure 3:
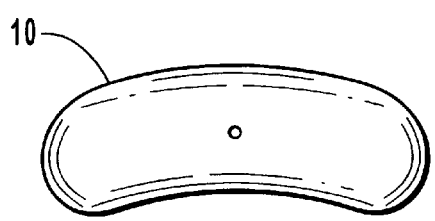
FIG. 3 is an end view of the hollow form of the device, including a view of the opening of the passageway leading to the exterior, illustrating an alternate external configuration.
Figure 4:
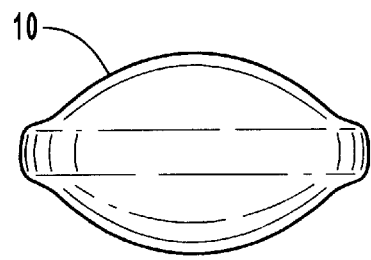
FIG. 4 is an end view of the solid form of the device for dispensing a beneficial agent into the oral cavity.
Figure 5:
FIG. 5 is an end view of the solid form of the device illustrating an alternate external configuration.
Figure 6:
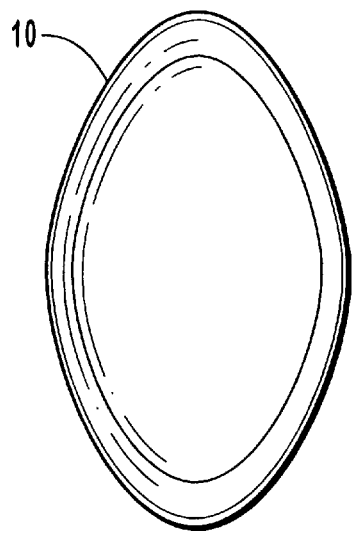
FIG. 6 is a general top view of a device for dispensing a beneficial agent into the oral cavity. Both hollow and solid forms are shown.

Turning now to the drawings, a device for delivering a beneficial agent into the oral cavity is shown in FIGS. 1, 2, 3, 4, 5, 6, 13, 14, and 15 and is indicated by the numeral 10. FIGS. 2 and 3 illustrates the hollow form of the device showing the opening of the passageway 16 leading to the exterior of the device.

Figure 7:
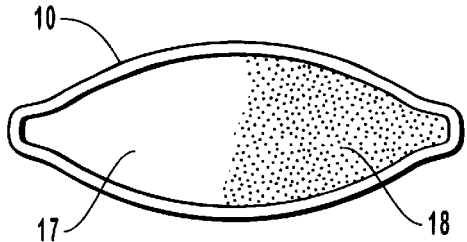
FIG. 7 is a view of the hollow form of the present invention in cross section.

FIG. 7 illustrates the hollow form of the device 10 comprised of an interior hollow compartment 17, and a beneficial agent 18.

Figure 8:
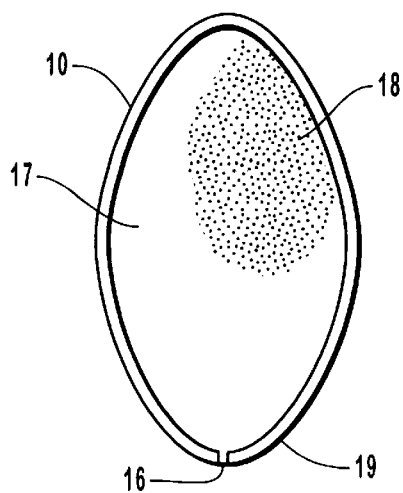
FIG. 8 is a view of the hollow form of the present invention in sagittal section.

FIG. 8 illustrates the hollow form or the device 10 comprised of an interior hollow compartment 17, a beneficial agent 18, a passageway 16 leading from the hollow compartment to the exterior of the device and the exterior wall 19 of the device 10.

Figure 9:
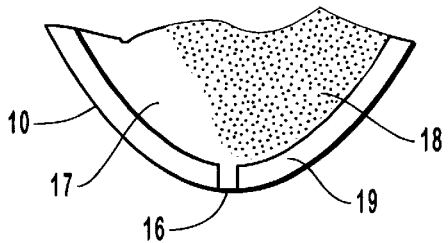
FIGS. 9, 11, and 12 are enlarged views of FIG. 8 showing a few of the different configurations of the passageway leading to the exterior of the hollow device.
Figure 11:
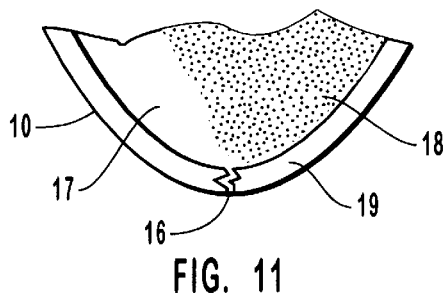
Figure 12:
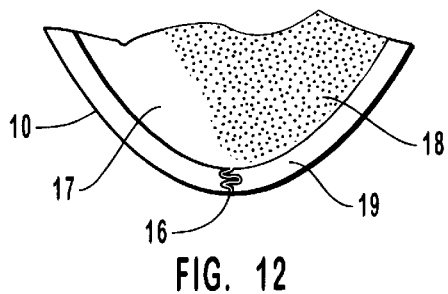

FIGS. 9, 11, and 12 illustrate areas of enlargement of the exterior wall 19 of FIG. 8. A few of the different configurations of the passageway 16 are illustrated. The purpose of the various configurations is to predetermine the rate at which the beneficial agent is released into the oral cavity.

Figure 13:
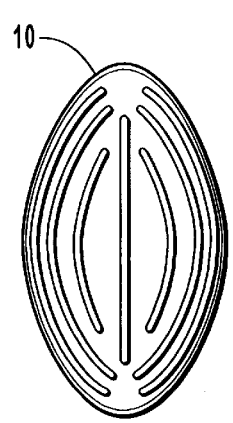
FIGS. 13, 14 and 15 are several views of the exterior of the present invention. In the drawings (which are not drawn to scale) like parts in related figures are identified by like so numerals.
Figure 14:
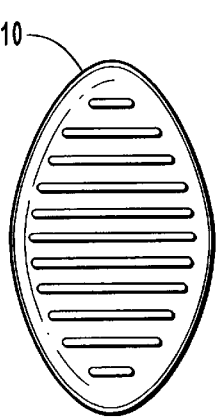
Figure 15:
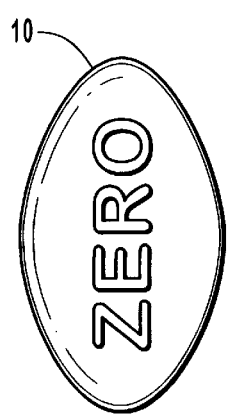

FIGS. 13, 14 and 15 illustrate several designs of the exterior of the device 10; the purpose of the designs are for increasing the exterior surface space of the device thereby increasing the amount of pleasant tasting agent that can be coated to the device.

This invention pertains to a device for delivering a beneficial agent or agents into the oral (buccal) cavity of a human or animal. More particularly, the device is comprised of one of two forms, 1) the hollow form is comprised of an inert wall and a hollow interior compartment containing the beneficial agent. A passageway in the wall connects the interior compartment with the exterior of the device. The size and configuration of the passageway determines the rate at which the agent or agents are released into the mouth, and 2) the solid form is comprised of combining a beneficial agent with a unique mixture that allows the beneficial agent to be slowly released into the mouth. External pressure on the device, such as sucking, squeezing or chewing influences the rate at which the agent or agents are released into the mouth.

The components of the device and the beneficial agent within the device, both active and inactive, should be on the GRAS list ("generally regarded as safe").

The types of components involved generally fall into the following categories:

1. Inert components of the device,
2. Flavorings, flavor enhancers, sweeteners and coloring,
3. Buffer forming agents,
4. Permeation enhancers, and
5. One or more therapeutic agents.

1. Inert Components of the Device:

The device is manufactured utilizing plastic, plastic combined with other materials, or similar compounds. All such materials comprising the device must be on the safe list as far as affecting humans or animals. Plastics are ideally suited for this device in that they can be shaped to conform to the shape of the oral cavity. Plastics are versatile in that they can be rubbery or rigid, having varying densities and textures.

Plastics consist of long chains of molecules called polymers; these chains are made up of repeating patterns of smaller molecules. Each of the smaller molecules forms a "link" in the polymer's chain.

Certain plastics can be combined with certain oils, both inert and otherwise, to lend elasticity and pliability to the end product. This combination of plastic and oil has the unique property of first absorbing beneficial agents during the production process and then secondly releasing slowly those beneficial agents into the mouth.

There are several types of plastics, however, thermoplastics can be melted and reformed again and again, thus, lending themselves to be most appropriate as a material to be used for the device.

Thermoplastic materials that potentially may be used for the device are: polyethylene, polyethyleneterephthalate, polyethylene/butylene, polyisoprene, polycarbonate, polypropylene, polystyrene, polytetrafluoroethylene, polyvinyl chloride, styrene, polyvinylidene, elastomeric polymers such as SEPTON or KRATON and nylon. These and other thermoplastics may be combined to create elastomeric polymers that when combined with certain oils create a unique compound. Oils such as mineral oil, olive oil, corn oil, soybean oil, safflower oil, cod liver oil, canola oil and other various oils can be used to combine with elastomeric and other plastics to create a compounds that have unique properties that lend themselves to be used in the device. Various oils can be combined with thermoplastics that produce a compound that will first: absorb flavors, flavor enhancers, coloring, sweeteners, permeation enhancers, buffer forming agents and one or more therapeutic agents; and secondly release these products into the mouth of a human or animal. This unique ability allows the solid form of the device to serve as a vehicle to release one or more beneficial agents into the mouth of a human or animal.

Manufactures use several processes to shape plastics. These processed are (1) Molding, (2) Casting, (3) Extrusion, (4) Calendering, (5) Laminating, (6) Foaming, (7) Thermoforming and (8) Others.

Injection molding is the most widely used method of molding thermoplastics, and is probably, along with extrusion, best suited for use in producing the device.

2. Flavorings, Flavor Enhancers, Sweeteners and Coloring:

A wide range of flavors are available for preparing good tasting and desirable medications within the scope of the present invention. These are required in order to mask the unpleasant taste of many drugs. Flavorings may be combined, as desired to produce a particular flavor mix which is compatible with a particular medication. Some of the confectioners' flavorings, or combination of flavorings, which have been used in the context of the present invention include vanilla, artificial vanilla, vanilla cream, mint, cherry, spearmint, peppermint, grape, coconut, chocolate, orange, menthol, licorice, lemon, lime, mixed fruit, root beer and butterscotch. Other flavorings known in the confectionery arts may also be acceptable because of the ease of combining the ingredients in the present invention. Any number of flavorings may be combined in any desired ratio in order to produce the specific desired taste characteristics required for any particular application; that is, flavor combinations may be varied in order to be compatible with the flavor change of any specific drug.

In order to produce a desirable color for the end product, artificial colorings may also be added to the composition. The flavorings described above are generally a white powder or liquid, as are the other major components. Therefore, additional coloring is necessary if a colored end product is desired. Coloring may also be important as a code to indicate the type and concentration of drug contained within a particular beneficial agent. Any type of color known to be "FD&C" certified, may be used to provide coloring to the product.

In order to provide a good tasting medication, sweeteners are preferably added to the composition. Sweeteners which are presently preferred include aspartase (NutraSweet), saccharin, acesulfame-K (Sunette or Sweet One), other artificial sweeteners, sugar and compressible confectioner's sugar. Other sweeteners such as fructose, dextrose, sorbitol, mannitol, corn syrup, xylitol, cyclamates, thaumatin, sucralose, alitame, PS99/PSIOO, monellin, clycyrrhizin, stevioside, miraculin, or L-sugars, etc., may also be acceptable for use within the scope of the present invention. Again, it is desirable that a sweetener or combination of sweeteners be obtained which is compatible with the drug and the other components such that a good tasting dosage-form is produced. Maltodextrin and cyclodextran may also be added to provide a better tasting composition. Maltodextrin and cyclodextran are generally employed in order to dissipate unpleasant flavors.

3. Buffer Forming Agents:

Buffering agents provide the ability to place the beneficial agent or medication in the mouth in a favorable pH environment for passage through the mucosal tissues of the mouth, pharynx, and esophagus. Buffering agents incorporated with a beneficial agent can be used to affect a pH change in the salival environment of the mouth in order to favor the existence of a unionized form of the agent which more readily moves through the mucosal tissues. In addition, appropriate pH adjustment can aid in producing a more palatable product with drugs which are either severely acidic (and thus sour) or severely basic (and thus bitter). As a result, a buffer system such as citric acid/sodium citrate has been found to be desirable for addition into the agent. A phosphate buffer system may also be used. The control of pH in view of drug pKa is very important. It is well known that most drugs are weak acids or weak bases and are present in solution in both the unionized and ionized forms. It has been found that the unionized portion of the drug is usually lipid soluble and can readily diffuse across the cell membrane. The ionized portion, conversely, is often lipid insoluble and in some instances, may not effectively penetrate the lipid membrane of the cell.

Whether a drug exists in the ionized or unionized form is largely dependent upon its pKa, and correspondingly on the pH of the solution. The present invention provides the unique ability to control the pH of the solution and thus the ratio of unionized form of the drug.

Ingredients can be added to a beneficial agent that is ionized, and therefore nondissolvable, to impart sufficient change in the pH of the saliva within the mouth such that the concentration of the unionized drug is increased. When the percentage of unionized drug is increased, transmucosal absorption of the drug is correspondingly increased. Therefore, by influencing the salival pH environment, it is possible to greatly improve the extent and rapidity of actual drug absorption, and therefore, the initial onset of the effect of the drug. Adding pH buffering systems (such as phosphate or citrate buffer systems) into the dosage-form can greatly facilitate delivery of the drug in the unionized (lipid soluble) form.

It will be appreciated that an additional advantage of the change of the pH may be that the taste characteristics of the drug can be improved. Drugs which are very high in pH typically are very bitter in taste; as the pH drops, the taste becomes less bitter, then salty, and may eventually become sour. Flavorings can more adequately improve the result, in addition to improving the drug delivery and buffering pH may also improve the taste characteristics of the composition.

Although the foregoing discussion has focused on the alteration of pH to enhance drug permeability by increasing the percentage of unionized drug forms, pH may enhance drug permeability by unknown mechanisms. For example, pH may effect drug molecular configuration which enhances drug permeability. Nonetheless, drug pH is often an important consideration in drug administration.

4. Permeation Enhancers Affecting Mucosal Membrane Penetration:

As previously discussed the pH of a beneficial agent may be altered to enhance drug permeability. As also discussed, most drugs are present in solutions in both the unionized and ionized forms. Generally only unionized, lipid soluble or lipophilic drugs readily diffuse across mucosal membranes. However, it has been found that ionized or nonlipophilic drugs may diffuse across mucosal membranes if treated with a permeation enhancer. It has also been found that permeability enhancers can significantly enhance the permeability of both lipophilic and nonlipophilic drugs.

Typical permeation enhancers include bile salts such as sodium cholate, sodium glycocholate, sodium deoxycholate, sodium glycodeoxycholate, taurodeoxycholate, sodium deoxycholate, sodium lithocholate chenocholate, chenodeoxycholate, ursocholate, ursodeoxycholate, hydroxycholate, dehydrocholate, glycochenocholate taurochenocholate, and taurochenodeoxycholate. Other permeation enhancers such as sodium dodecyl sulfate ("SDS"), dimethyl sulfoxide ("DMSO"), sodium lauryl sulfate salts, and other derivatives of saturated and unsaturated fatty acids, surfactants, bile salt analogs, derivatives of bile salts. or such synthetic permeation enhancers as described in U.S. Pat. No. 4,746,508 may also be used.

It is almost impossible to predict which enhancer will work best for a given drug. For each individual drug, only experiments can tell which enhancer is the most suitable. However, it is generally believed that bile salts are good for nonlipophilic drugs while long chain fatty acids, their salts, derivatives, and analogs are more suitable for lipophilic drugs. DMSO, SDS, and medium chain fatty acids (C-8 to about C-14), their salts. derivatives, and analogs may work for both nonlipophilic and lipophilic drugs.

The effectiveness of some enhancers may vary depending on the chemical compound to be permeated. One particular enhancer may work very well on one drug but may not have any effect on another drug. For example, oleic acid greatly improves the transdermal permeability of estradiol, a very lipophilic drug, but oleic acid does not have any effect on the transmucosal permeability of glucose, a very hydrophilic drug. Although it is possible to speculate whether a given enhancer may or may not enhance a given drug's permeability, the actual effectiveness of an enhancer should be verified experimentally.

5. Beneficial Agents:

Many drugs, herbs and compounds lend themselves to be used in the delivery device for transmucosal dosage. Beneficial agents include, but are not limited to: an appetite pacifier, an antibiotic, an antifungal, an anti-yeast, an antiviral, an antihistamine, a vitamin, a multivitamin, a mineral, a multimineral, a multi-vitamin/mineral, a sedative, a tranquilizer, an analgesic, an anesthetic, a local anesthetic, an anesthetic antagonist, an anti-inflammatory, a steroid, a nonsteroid anti-inflammatory, a lipophilic, a nonlipophilic, an antidote, an antispasmodic, a hormone, a blood pressure decreasing drug, a hypotensive, a hypertensive, an antihypertensive, a coagulant, a blood thinner, a diuretic, an antidiuretic, a vasodilator, a heart stimulant, an antiarrhythmic, a cardiovascular acting drug, an antianginal, an antithrombotic, an anti-hyperglycemic drug, a blood sugar decreasing drug, an antiacid, an anti-shock drug, a smooth muscle stimulant, a smooth muscle relaxer, a stimulant, a depressant, an endorphin, an antiemetic, an antidiarrheal, a beta blocker, an ACE inhibitor, an anti-parkinson disease drug, a bronchodilator, an anti-migraine, an oxytocic, a macromolecular, an amino acid, a polysaccharide, a polypeptide, an antigen, a nucleoside, an antibody, an enzyme, an antienzyme, a central nervous system acting drug, an anticonvulsant, a renal acting drug, an anxiolytic, an amnestic, an anti-plaque agent, an antipruritic, an antisecretory, an atropine drug, a scopolamine, a permeation enhancer, an alcohol, a 5-HT agonist, a ganglionic stimulant, an antimescarinic, nicotine, a nicotine compound, a synthetic nicotine, an anti-smoking drug, a bone densilier, an anti-ulcer drug, an anticolitis drug, an anticystitis drug, a urinary acidifier, a urinary incontinence drug, an anticancer drug, an anti-baldness drug, an allergy suppressant, an anti-pneumonia drug, a cystic fibrosis drug, a multiple sclerosis drug, a chronic fatigue syndrome drug, an anti-Down syndrome drug, a psychological illness drug, an anti-addiction drug, a behavior disorder drug, an anxiety suppressant, a compulsive behavior suppressant, a cataract drug, an osteoporosis drug, an AIDs suppressant, an immune system stimulant, a male or female libido drug, a male or female sex hormone suppressant and any other beneficial drugs.

Further Embodiments of the Invention Include:

1. A non-dissolvable device that has a size and shape adapting it to be comfortably retained in the mouth for extended periods of time.
2. A device designed to release a beneficial agent into the mouth of a human or animal for use in transmucosal delivery of the agent to a patient or individual.
3. A pharmacologically effective dose of a drug being capable of absorption through mucosal tissues of the mouth, pharynx, and esophagus, the pharmacologically effective dose of the drug being contained by the nondissolvable device.
4. A drug-containing dosage-form for use in transmucosal delivery of the drug to a patient as defined in claim 1, wherein the nondissolvable drug containment device may be formulated in one of two forms: 1) is a chamber defined by an impermeable barrier, said permeable barrier having a passageway size and configuration designed to allow a predetermined dosage to be delivered to the mouth for transmucosal absorption under optimum conditions, and 2) a second form, the solid form comprised of combining a beneficial agent with a mixture of thermoplastic polymers and oils that allows the beneficial agent to be slowly released into the mouth.
5. The nondissolvable drug containment device is designed to specifically contain a drug, a mixture of drugs, a compound, or mixture of compounds for use in the device defined in claim 1, wherein the drug or compound is, but not limited to: an appetite pacifier, an antibiotic, an antifungal, an anti-yeast, an antiviral, an antihistamine, a vitamin, a multivitamin, a mineral, a multimineral, a multi-vitamin/mineral, a sedative, a tranquilizer, an analgesic, an anesthetic, a local anesthetic, an anesthetic antagonist, an antiinflammatory, a steroid, a nonsteroid antiinflammatory, a lipophilic, a nonlipophilic, an antidote, an antispasmodic, a hormone, a blood pressure decreasing drug, a hypotensive, a hypertensive, an antihypertensive, a coagulant, a blood thinner, a diuretic, an antidiuretic, a vasodilator, a heart stimulant, an antiarrhythmic, a cardiovascular acting drug, an antianginal, an antithrombotic, an anti-hyperglycemic drug, a blood sugar decreasing drug, an antiacid, an anti-shock drug, a smooth muscle stimulant, a smooth muscle relaxer, a stimulant, a depressant, an endorphin, an antiemetic, an antidiarrheal, a beta blocker, an ACE inhibitor, an anti-parkinson disease drug, a bronchodilator, an anti-migraine, an oxytocic, a macromolecular, an amino acid, a polysaccharide, a polypeptide, an antigen, a nucleoside, an antibody, an enzyme, an antienzyme, a central nervous system acting drug, an anticonvulsant, a renal acting drug, an anxiolytic, an amnestic, an anti-plaque agent, an antipruritic, an antisecretory, an atropine drug, a scopolamine, a permeation enhancer, an alcohol, a 5-HT agonist, a ganglionic stimulant, an antimescarinic, an anti-smoking drug, nicotine, a nicotine compound, a synthetic nicotine, a bone densifier, an anti-ulcer drug, an anticolitis drug, an anticystitis drug, a urinary acidifier, a urinary incontinence drug, an anticancer drug, an anti-baldness drug, an allergy suppressant, an anti-pneumonia drug, a cystic fibrosis drug, a multiple sclerosis drug, a chronic fatigue syndrome drug, an anti-Down syndrome drug, a psychological illness drug, an anti-addiction drug, a behavior disorder drug, an anxiety suppressant, a compulsive behavior suppressant, a cataract drug, an osteoporosis drug, an AIDs suppressant, an immune system stimulant a male or female libido drug, a male or female sex hormone suppressant and any other beneficial drugs or agents.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An lozenge comprising:
   a mixture of a thermoplastic, an oil, and a beneficial agent that allows the beneficial agent to be released upon application of a pressure upon an external surface of the mixture, said thermoplastic being inert to the salival environment of a mammal.
2. The lozenge as defined in claim 1, wherein the mixture further comprises a permeation enhancer.
3. The lozenge as defined in claim 1, wherein said thermoplastic is selected from a group consisting of polyethylene, polyethylene terephthalate, polyethylene/butylene, polyisoprene, polycarbonate, polypropylene, polystyrene, polytetrafluoroethylene, polyvinyl chloride, styrene, polyvinylidene, and an elastomeric polymer.
4. The lozenge as defined in claim 3, wherein said elastomeric polymer is nylon.
5. The lozenge as defined in claim 1, wherein said oil is selected from a group consisting of mineral oil, olive oil, corn oil, soybean oil, safflower oil, cod liver oil, and canola oil.
6. The lozenge as defined in claim 1, wherein said mixture has a rigid exterior surface.
7. The lozenge as defined in claim 6, wherein the rigid exterior surface is shaped to conform to a portion of the shape of a body cavity of a mammal.
8. The lozenge as defined in claim 1, wherein said mixture has a non-rigid exterior surface.
9. The lozenge as defined in claim 8, wherein the non-rigid exterior surface is malleable.
10. The lozenge as defined in claim 1, wherein the mixture further comprises at least one of a flavoring, a flavor enhancer, a sweetener, and a coloring.

11. The lozenge as defined in claim 1, wherein the mixture further comprises:
a buffering agent for changing the pH of the salival environment of the mammal; and wherein the beneficial agent provides a pharmacological effect via transmucosal delivery.

12. The lozenge as defined in claim 11, wherein said transmucosal delivery of said beneficial agent is adapted for administration by absorption through mucosal tissues of the mouth, pharynx, and esophagus of the mammal.

13. The lozenge as defined in claim 11, wherein said mixture releases said beneficial agent for said transmucosal delivery into the oral cavity of a mammal as said mammal sucks, squeezes, or chews on the mixture.

14. The lozenge as defined in claim 1, wherein the buffering agent includes at least one of citric acid and sodium citrate.

15. The lozenge as defined in claim 1, wherein the buffering agent includes a phosphate.

16. The lozenge as defined in claim 2, wherein the permeation enhancer is selected from the group consisting of oleic acid, bile salts, sodium cholate, sodium glycocholate, sodium deoxycholate, sodium glycodeoxycholate, taurodeoxycholate, sodium deoxycholate, sodium lithocholate chenocholate, chenodeoxycholate, ursocholate, ursodeoxycholate, hydroxycholate, dehydrocholate, glycochenocholate taurochenocholate, taurochenodeoxycholate, sodium dodecyl sulfate ("SDS"), dimethyl sulfoxide ("DMSO"), sodium lauryl sulfate salts, derivatives of saturated fatty acids, derivatives of unsaturated fatty acids, surfactants, derivatives of bile salts, long chain fatty acids, long chain fatty acids salts, long chain fatty acids derivatives, and medium chain fatty acids in a range from about C-8 to about C-14 including their salts.

17. An lozenge comprising:
a housing having an exterior surface that is composed of a mixture of an oil and a thermoplastic that is non-dissolvable in and impermeable to the saliva of a mammal;
a cavity within the housing;
a wall separating the cavity from the exterior surface of the housing;
a beneficial agent including a liquid;
a passage way for providing fluid communication of the beneficial agent from the cavity to the exterior surface of the housing.

18. The lozenge as defined in claim 17, wherein the beneficial agent is adapted for transmucosal absorption in the tissues of a body cavity of a mammal.

19. An lozenge for administering a beneficial agent transmucosally, said lozenge comprising:
a housing impermeable to and non-dissolvable in bodily fluids of a mammal and composed of a combination of a thermoplastic and an oil;
a cavity defined within the housing;
a beneficial agent including a liquid within the cavity;
a lumen in fluid communication between the cavity and the exterior of the housing for communicating the beneficial agent from the cavity to the outside of the housing.

20. The lozenge as defined in claim 19, wherein the housing:
is resilient to the application of pressure thereto; and
expresses said beneficial agent therefrom through said lumen upon application of pressure to said housing.

21. The lozenge as defined in claim 19, wherein the housing has an exterior surface having thereon at least one of raised and recessed portions.

22. The lozenge as defined in claim 19, wherein the thermoplastic and the oil are non-dissolvable in a salival environment of a mammal.

23. The lozenge as defined in claim 19, wherein said beneficial agent includes at least one of a lipophilic drug and a non-lipophilic drug adapted to be administered transmucosally.

24. The lozenge as defined in claim 19, wherein said beneficial agent is adapted to be transferable across the mucosal tissues of a body cavity of a mammal.

25. The lozenge as defined in claim 19, wherein said beneficial agent is adapted to be permeable to the mucosal tissues of the mouth, pharynx and esophagus of a mammal upon application of pressure to the exterior surface of the housing.

26. The lozenge as defined in claim 19, wherein the beneficial agent further comprises:
at least one of a flavoring, a flavor enhancer, a sweetener, and a coloring; and
an buffering agent for changing the pH of the salival environment of the mammal,
wherein the beneficial agent provides a pharmacological effect via transmucosal delivery.

27. The lozenge as defined in claim 19, wherein said thermoplastic is selected from a group consisting of polyethylene, polyethylene terephthalate, polyethylene/butylene, polyisoprene, polycarbonate, polypropylene, polystyrene, polytetrafluoroethylene, polyvinyl chloride, styrene, polyvinylidene, and an elastomeric polymer.

28. The lozenge as defined in claim 27, wherein said elastomeric polymer is nylon.

29. The lozenge as defined in claim 19, wherein said oil is selected from a group consisting of mineral oil, olive oil, corn oil, soybean oil, safflower oil, cod liver oil, and canola oil.

30. The lozenge as defined in claim 26, wherein the beneficial agent further comprises a permeation enhancer.

31. The lozenge as defined in claim 19, wherein at least one of said thermoplastic and said oil:
is adapted to absorb said beneficial agent; and
releases said beneficial agent into a body cavity of a mammal upon application of pressure to the exterior surface of said housing.

32. The lozenge as defined in claim 26, wherein the buffering agent includes at least one of citric acid and sodium citrate.

33. The lozenge as defined in claim 26, wherein the buffering agent includes a phosphate.

34. The lozenge as defined in claim 30, wherein said permeation enhancer is selected from the group consisting of oleic acid, bile salts, sodium cholate, sodium glycocholate, sodium deoxycholate, sodium glycodeoxycholate, taurodeoxycholate, sodium deoxycholate, sodium lithocholate chenocholate, chenodeoxycholate, ursocholate, ursodeoxycholate, hydroxycholate, dehydrocholate, glycochenocholate taurochenocholate, taurochenodeoxycholate, sodium dodecyl sulfate ("SDS"), dimethyl sulfoxide ("DMSO"), sodium lauryl sulfate salts, derivatives of saturated fatty acids, derivatives of unsaturated fatty acids, surfactants, derivatives of bile salts, long chain fatty acids, long chain fatty acids salts, long chain fatty acids derivatives, and medium chain fatty acids in a range from about C-8 to about C-14 including their salts.

* * * * *